(12) United States Patent
Yang et al.

(10) Patent No.: US 8,764,448 B2
(45) Date of Patent: Jul. 1, 2014

(54) ROBOTIC DEVICE FOR USE IN IMAGE-GUIDED ROBOT ASSISTED SURGICAL TRAINING

(75) Inventors: Tao Yang, Sangapore (SG); Liangjing Yang, Singapore (SG); Jiang Liu, Singapore (SG); Chee Kong Chui, Singapore (SG); Weimin Huang, Singapore (SG); Jing Zhang, Singapore (SG); Jiayin Zhou, Singapore (SG); Beng Hai Lee, Singapore (SG); Ngan Meng Tan, Singapore (SG); Wing Kee Damon Wong, Singapore (SG); Fengshou Yin, Singapore (SG); Kin Yong Chang, Singapore (SG); Yi Su, Singapore (SG)

(73) Assignees: Agency for Science, Technology and Research, Singapore (SG); National University Hospital (s) PTE Ltd, Singapore (SG); National University of Singapore, Singapore (SG)

( * ) Notice: Subject to any disclaimer, the term of this patent is extended or adjusted under 35 U.S.C. 154(b) by 0 days.

(21) Appl. No.: 13/820,065

(22) PCT Filed: Sep. 1, 2011

(86) PCT No.: PCT/SG2011/000302
§ 371 (c)(1),
(2), (4) Date: May 16, 2013

(87) PCT Pub. No.: WO2012/030304
PCT Pub. Date: Mar. 8, 2012

(65) Prior Publication Data
US 2013/0224710 A1    Aug. 29, 2013

(30) Foreign Application Priority Data

Sep. 1, 2010    (SG) .................................. 20106367-5

(51) Int. Cl.
*G09B 23/28*    (2006.01)
*A61B 17/00*    (2006.01)
*G06G 7/58*    (2006.01)
*A61B 19/00*    (2006.01)

(52) U.S. Cl.
CPC ............ *G09B 23/28* (2013.01); *A61B 19/2203* (2013.01)
USPC ................................. 434/262; 606/1; 703/11

(58) Field of Classification Search
CPC ............................ G09B 23/28; A61B 19/2203
USPC ................................. 434/262; 606/1; 703/11
See application file for complete search history.

(56) References Cited

U.S. PATENT DOCUMENTS

| 7,023,423 | B2 | 4/2006 | Rosenberg |
| 2007/0172803 | A1 | 7/2007 | Hannaford et al. |
| 2009/0009492 | A1 | 1/2009 | Gregorio et al. |

FOREIGN PATENT DOCUMENTS

WO    2012/030304 A1    3/2012

OTHER PUBLICATIONS

Kang, H. et al., EndoBot: a Robotic Assistant in Minimally Invasive Surgeries, Proceedings of the 2001 IEEE International Conference on Robotics & Automation, May 21-26, 2001, pp. 2031-2036, vol. 2, Seoul, Korea.

(Continued)

*Primary Examiner* — Xuan Thai
*Assistant Examiner* — Jerry-Daryl Fletcher
(74) *Attorney, Agent, or Firm* — Wolf, Greenfield & Sacks, P.C.

(57) ABSTRACT

A robotic device for use in image-guided robot assisted surgical training, the robotic device comprising a manual interface structure configured to simulate handling of a surgical tool; a translational mechanism for translational motion of the manual interface structure; a rotational mechanism for rotational motion of the manual interface structure; and a spherical mechanism configured to decouple the orientation of the manual interface structure into spatial coordinates, wherein a linkage between the rotational mechanism, the rotational mechanism and the spherical mechanism, and the manual interface structure are disposed on opposing sides of an intersection of a pitch axis and a yaw axis of the spherical mechanism.

15 Claims, 7 Drawing Sheets

(56) References Cited

OTHER PUBLICATIONS

Kang, H. et al., Robotic Assistants Aid Surgeons During Minimally Invasive Procedures, IEEE Engineering in Medicine and Biology, Jan./Feb. 2001, pp. 94-104, vol. 20, issue 1.

da Vinci Surgical System by Intuitive Surgical Inc., http://www.intuitivesurgical.com/products/davinci_surgical_system/ [last accessed Aug. 20, 2013].

Lap Mentor, II by SimBionix, available before the priority date of this application. http://simbionix.com/simulators/lap-mentor/ [Aug. 20, 2013].

SimPraxis Laparoscopic Cholecystectomy Trainer by Red Llama, available before the priority date of this application. http://redllamastore.com/products/simpraxis-laparoscopic-cholecystectomy-trainer [last accessed Aug. 20, 2013].

The LaparoscopyVR Virtual-Reality System by Immersion, Available before the priority date of this application. Product Release Information. Jun. 6, 2007. http://ir.immersion.com/releasedetail.cfm?ReleaseID=247425 [last accessed Sep. 9. 2013].

Xitact IHP Instrument Haptic Port by Mentice, in Samur, Performance Metrics for Haptic Interfaces. Springer, 2012; 14-16.

Baheti et al., RoSS: Virtual Reality Robotic Surgical Simulator for the da Vinci Surgical System. Symposium on Haptic Interfaces for Virtual Environment and Teleoperator Systems. Mar. 13-14, 2008. Reno, Nevada, USA. 479-480.

Baur et al., Virgy: a virtual reality and force feedback based endoscopic surgery simulator. Swiss Federal Institute of Technology. 1998. Accessed online via http://www.virtualsurgery.vision.ee.ethz.ch/Xitact/LapChole#AdditionalInfo [last accessed Sep. 9, 2013].

Dede et al., Design of a haptic device for teleoperation and virtual reality systems. IEEE Conference on Systems, Man and Cybernetics. Oct. 2009. San Antonio, Texas, USA. 3623-8.

Voyles et al., A practical approach to laparoscopic cholecystectomy. American Journal of Surgery. Mar. 1991; 161(3):365/70.

Zheng et al., Kinematic analysis of a hybrid serial-parallel manipulator. International Journal of Advanced Manufacturing Technology. 2004; 23:925-30.

ROBOTIC DEVICE FOR USE IN IMAGE-GUIDED ROBOT ASSISTED SURGICAL TRAINING

RELATED APPLICATIONS

This application is a U.S. National Stage application under §371 of International Application No. PCT/SG2011/000302, filed Sep. 1, 2011, which claims priority to Singapore Application No. 201006367-5, filed Sep. 1, 2010, the contents of all of which are incorporated herein by reference in their entirety.

FIELD OF INVENTION

The present invention broadly relates to a robotic device for use in image-guided robot assisted surgical training.

BACKGROUND

The advantages of laparoscopic surgery have made this technology the preferred choice for most surgeries. 95 percent of cholecystectomy were performed laparoscopically. However, due to the nature of laparoscopic surgery, intensive training is required before the surgeon is confident to perform the surgery on patients. Traditionally, surgical training is done with the 'master-apprentice' strategy. The trainee surgeon has to learn the surgical procedure by repeating the steps as performed by the master surgeon after having observed his/her master surgeon performed it several times. Some times the master surgeon has to "hold" the trainee's hands in order to show the trainee a subtle movement. With increasing complexity of the surgical operations nowadays, it becomes increasingly dangerous for the trainee surgeon to 'learn' while operating on a real patient despite being supervised during the operation.

Currently, there are several surgical simulation systems that provide training features to build fundamental skills for laparoscopic surgery. Although operative scenarios are provided in the surgical simulation instruments, there are some limitations. These include the lack of varieties. Certain maneuvers by an experienced surgeon cannot be easily taught to the trainee surgeon. Current simulation systems are passive in nature, and hence, act as a practicing environment rather than an active teaching tool. A good surgical training system is associated with rapid learning curve among experienced surgeons from multiple surgical disciplines. It should transfer the experiences from the operation room to other surgeons, and hence, sharpen the surgical skills of surgeons.

LaparoscopyVR and Lap Mentor II developed by Immersion and Simbionix respectively provide facilities to gain hands-on experiences. However, these training methods are designed for medical staff with some basic skills and experiences in laparoscopic surgery. Since all motions of the surgical tool are passive without motion guidance, the trainee surgeon has to perform the task based on his/her own skills. The simulation instruments are incapable of providing active teaching, since the simulation instruments do not provide physical motion guiding.

Xitact™ IHP, developed by Mentice, is a haptic simulation hardware for minimally invasive surgical procedures, such as laparoscopy, nephrectomy, arthroscopy, and even cardiac surgery. Action and reaction are synchronized so that the resistance of an actual organ is recreated in the 'touch' sensations experienced by the user. Although the motion of Xitact™ IHP is tracked, the Xitact IHP does not actively drive the surgical tool to move autonomously, therefore it is not able to provide active guidance to the user. As it is incapable of varying the force output, the haptic feedback for tool-tissue interaction is not realistic.

EndoBot, developed by Rensselaer Polytechnic Institute, is designed to assists surgeons during minimally invasive procedures. The model of motion of EndoBot can be passive and active, and the EndoBot provides with encoder for tracking of motion, but it does not provide haptic feedback. The robot is able to assist the surgeon to complete some specific tasks, such as suturing, or constraining manual suturing in certain path. The robot does not provide any feature in training. Although the mechanism is designed with mobility that mimics the kinematic motion of a laparoscopic surgery device, its actuating mechanism is meant to be driven by motors with high torque range like most assistive devices. For instance, the use of a lead screw thread for the translational axis makes back driving difficult when the device is in passive mode.

U.S. Pat. No. 7,023,423 "Laparoscopic Simulation Interface" proposed a method and apparatus for laparoscopic surgery training interface. The use of its gimbal mechanism for pitch and yaw control of the tool can provide structural stability, but compromises on workspace efficiency. The mechanism was designed such that parts of the linkage can be exposed beyond the incision point marked by the intersection of the two pitch and yaw axes. The intrusion of mechanical linkage into the user operational workspace is undesirable in a user-centric simulator. Also, the pitch and axes are each achieved by connecting three members "in series", which requires a large work space for implementation, and may increase the possibility of mechanical failure. In addition, like most other closed-loop linkages, the mapping of the joint space to task space and vice versa is non-trivial.

Example embodiments of the present invention therefore seek to provide a method and system that address at least one of the above mentioned problems.

SUMMARY

In accordance with a first aspect of the present invention there is provided a robotic device for use in image-guided robot assisted surgical training, the robotic device comprising a manual interface structure configured to simulate handling of a surgical tool; a translational mechanism for translational motion of the manual interface structure; a rotational mechanism for rotational motion of the manual interface structure; and a spherical mechanism configured to decouple the orientation of the manual interface structure into spatial coordinates, wherein a linkage between the rotational mechanism, the rotational mechanism and the spherical mechanism, and the manual interface structure are disposed on opposing sides of an intersection of a pitch axis and a yaw axis of the spherical mechanism.

The spherical mechanism may comprise first and second substantially orthogonal rotatable spherical arches, wherein movement of the manual interface structure drives the first and second spherical arches.

The spherical mechanism may comprise first and second pairs of an actuator and a sensor for each of the first and second arches.

The translational mechanism may comprise a third pair of an actuator and a sensor.

The rotational mechanism may comprise a fourth pair of an actuator and a sensor.

The manual user interface may comprise an open-and-close mechanism to simulate opening and closing of the surgical tool.

The open-and-close mechanism may comprise a fifth pair of an actuator and a sensor.

The sensors may be configured to record operation of the manual interface structure by a user.

The actuators may be configured to drive the manual interface to reproduce a recorded operation of the manual interface structure.

The manual interface structure may comprises a shaft coupled to each of the translational, rotational, and spherical mechanisms.

The linkage may comprise a slider moveable within the first and second spherical arches and configured to couple the shaft to the first and second spherical arches.

The slider may be configured to enable rotational and translational movement of the shaft relative to the first and second spherical arches.

The shaft may be coupled to the translational mechanism by way of a track and gear coupling.

The shaft may be coupled to a rotational axis of the rotational mechanism.

The spherical mechanism may comprise a base of the robotic device supporting the first and second spherical arches, the manual interface structure and the translational and rotational mechanisms.

BRIEF DESCRIPTION OF THE DRAWINGS

Embodiments of the invention will be better understood and readily apparent to one of ordinary skill in the art from the following written description, by way of example only, and in conjunction with the drawings, in which:

FIG. 3a) and b) illustrate a hardware design of the robotic device according to an example embodiment.

FIG. 4a) and b) show a hardware design of a component of the robotic device according to an example embodiment.

DETAILED DESCRIPTION

In example embodiments, a robotic device, as part of the image-guided robot assisted surgical training system, is designed to learn from the master surgeon, and interact with the trainee surgeon to teach him/her the skills from the master surgeon. A real patient anatomical model with targeted illness is embedded in image-guided robot assisted surgical training system; a master surgeon operates on the virtual patient model through the robotic device. The robotic device records the procedure of a surgery performed by the master surgeon, and replays this procedure to the trainee surgeon. Given active guidance based on the replayed motion, the trainee surgeon is provided with a way to learn the skills, including tactile motion from the master surgeon indirectly. The learning process can be repeated without exhausting the master surgeon.

When the trainee surgeon is confident enough, he/she can perform the surgery on his/her own. The motion of the surgical tools can be recorded for the purpose of evaluation.

Example embodiments can provide both passive and active model which allow the trainee surgeon to learn and practice through indirect physical guiding from master surgeons. In the passive mode, the robot is back driven by user (i.e. master surgeon or trainee). On the other hand, the robot simulates a surgery autonomously in the active mode, which can also be used as guidance to a trainee surgeon. The Robotic robotic device provides with encoder for tracking of motion and also provides with haptic feedback.

The robotic trainer in example embodiments passes operation room experiences to trainee surgeons, and sharpens the skills of surgeons. The advantageous example embodiments of the robotic device lie in the features that satisfy a one-stop training simulator. This includes the integration of active robotic guidance which is lacking in existing passive simulators, and the user centric design.

In example embodiments, the active robotic guidance can offer physical motion guided learning on top of the virtual simulator. The active robotic guidance preferably teaches the expertise and experiences obtained from operation room to its user. The user centric design provides a realistic physical platform for laparoscopic surgical simulation. With the actuation system built beneath the abdominal model, the training workstation is an exact mimic of the work environment.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Figure 1:
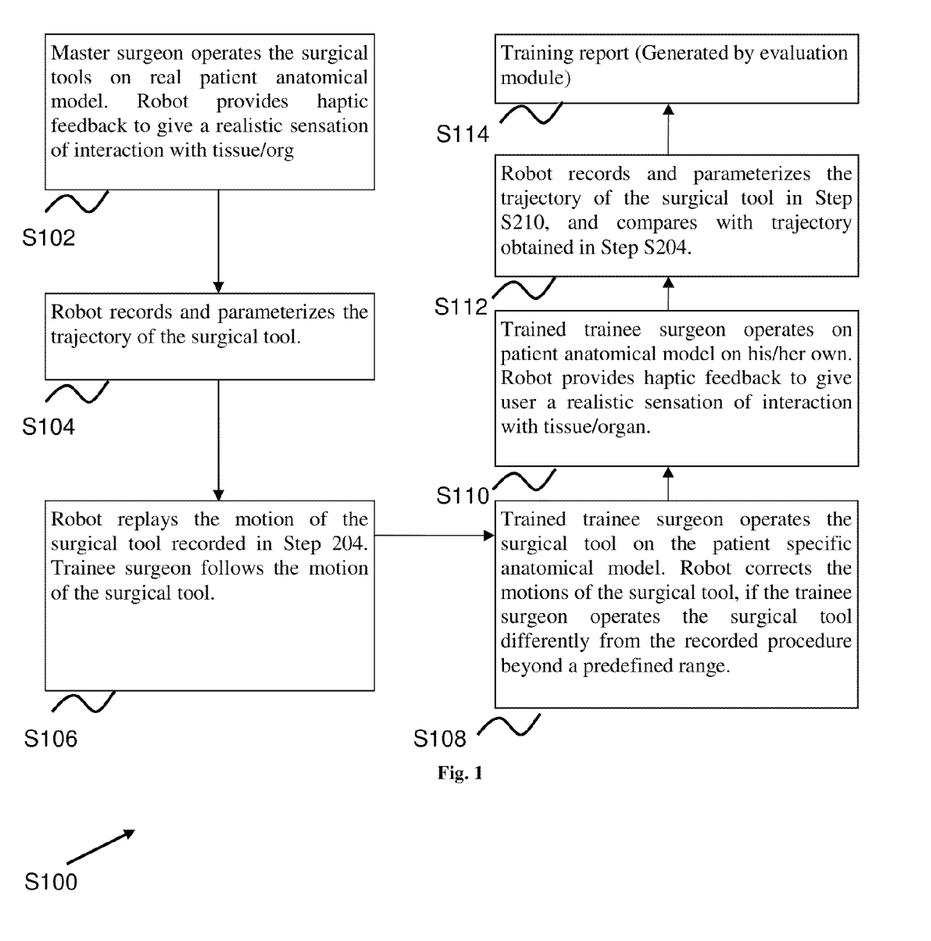
FIG. 1 illustrates an architecture of the robotic device for Image-Guided Robot Assisted Surgical training system according to an example embodiment.
Figure 2:
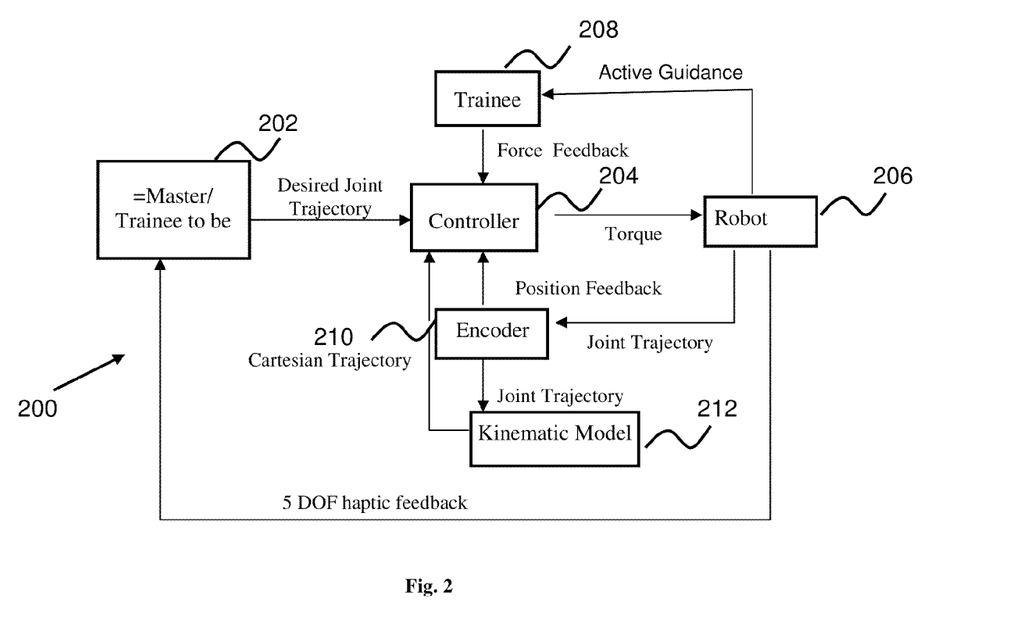
FIG. 2 shows a flowchart illustrating working process of robotic surgical training, according to an example embodiment.

FIG. 2 shows a flowchart S100 illustrating working process of robotic surgical training, according to an example embodiment.

It has been recognized by the inventors there are preferably several subtasks to the working process of robotic surgical training, as illustrated in FIG. 2. At Step S102, a master surgeon operates the surgical tools on real patient anatomical model. Robot provides haptic feedback to give a realistic sensation of interaction with tissue/organ.

Next, there are four modes of operation for the robotic device, namely Record (Step S104), Replay (Step S106), Robotic assisted teaching (Step S108, Step S110, Step S112), and Trainee mode (Step S114). A patient specific anatomical model generated by image processing techniques can be loaded in the image-guided robot assisted surgical training system. All four operation modes work on the virtual patient specific anatomical model.

In Record mode (Step S104), the robot records and parameterizes the trajectory of the surgical tool. The robot is passively operated by the master surgeon. The surgical tool is operated by the user manually. Motion of the surgical tool is decoupled into roll, pitch, yaw, translation and open/close of surgical tool handle. All these information is recorded to reconstruct the trajectory of the surgical tool. In order to provide the user with realistic sensation (haptic), a proper control system/controller can be used to generate the sensation of tool-environment interaction based on tissue's biomechanics model.

In Replay mode (Step S106), the robot replays the motion of the surgical tool recorded in Step S104. A trainee surgeon follows the motion of the surgical tool. The robot actively drives the surgical tool. The trainee surgeon can hold the handle of the surgical tool, and follow the trajectory of the surgical tool to learn the procedure of a recorded surgery.

Robotic assisted teaching mode (Step S108) is for a trainee surgeon who has gained confidence from the replay mode. The trainee surgeon is allowed to operate on the patient specific anatomical model with the surgical procedure learnt in the replay mode. At Step S108, a trained trainee surgeon operates the surgical tool on the patient specific anatomical model. The trajectory (namely: L) of the surgical tool is tracked. In the meantime, this trajectory is compared to the trajectory (namely: M) acquired in the record mode. If the difference between trajectory L and trajectory M exceed a predefined range, the robot corrects the motions of the surgical tool by providing force feedback in the corresponding direction in order to follow trajectory M. In this mode, the trainee surgeon is given some freedom to perform the surgery with learnt procedures. At Step S110, the trained trainee surgeon operates on patient anatomical model on his/her own.

Trainee mode (Steps S110-S114) allows the trainee surgeon to operate on the anatomical model with the learnt surgical procedure on his/her own accord. The motion of the surgical tool is recorded for evaluation purpose. At Step S112, the robot records and parameterizes the trajectory of the surgical tool in Step S110, and compares with trajectory obtained in Step S104. In this mode, the robot provides haptic feedback to give the user a realistic sensation of interaction with tissue/organ same as in the record mode. At Step S114, a training report is generated by an evaluation module.

FIG. 2 illustrates the functional architecture of the proposed robotic system 200 according to an example embodiment. A master surgeon/trainee will operate the robotic device manually 202. Motion of the surgical tool is decoupled into roll, pitch, yaw, translation and open/close of surgical tool handle. All these information is recorded to reconstruct the desired joint trajectory of the robotic device, and the desired joint trajectory information is inputted to a controller 204, which can be used to generate the sensation of tool-environment interaction based on tissue's biomechanics model. On the other hand, a robot 206 provides the master/trainee surgeon with 5 DOF haptic feedback. In robotic assisted training mode, the trainee 208 provides the controller 204 with motion feedback for further evaluation. In addition to providing active guidance to the trainee 208, the robot 206 also inputs the joint trajectory information to an encoder 210, and the encoder 210 provides the positive feedback to the controller 204 and also input the joint trajectory information to a kinematic model 212, which transforms the joint trajectory information into Cartesian trajectory information. The Cartesian trajectory information is inputted to the controller 204. The controller 204 outputs the torque information to the robot 206 and adjusts the robot 206's movement.

Note that the diagram reflects the overall functional architecture without considering a specific operation mode. Hence certain elements in the diagram may not be relevant in certain modes. For instance, the system may not acquire force feedback from the trainee surgeon to the controller during the replay mode. Force feedback may however be input to the controller to achieve the defined servo stiffness in the robotic assisted teaching mode. In the case of the record and the trainee mode, the robot can provide a 5 DOF haptic feedback to the user. The robot operates as a virtual simulator with haptic interface in record and trainee mode.

FIG. 3a) and b) illustrate the hardware design of the robotic device 300 according to an example embodiment.

The robotic device 300, as depicted in FIGS. 3a) and b) is designed to learn from the master surgeon, and interact with the trainee surgeon to teach him/her the skills from the master surgeon. The robotic device is designed as shown in FIG. 3a. The robotic device 300 provides 4 degrees of freedom (DOF), including pitch DOF, yaw DOF, roll DOF and translate DOF with open/close of tool handles, see details about mobility in FIG. 3b. The robot in the example embodiment consists of a component (see FIG. 4b) for details), actuators (306, 308, 310, 312, 314) with sensors (316, 318, 320, 322, 324 in FIG. 3a), and spherical mechanism (326 in FIG. 3a). The component 302 is the basic training interface for both master surgeon and trainee surgeon. However, the component needs some modification based on the normal surgical tool 402 in FIG. 4a) to cooperate with other working mechanism in the robot.

Figure 3:
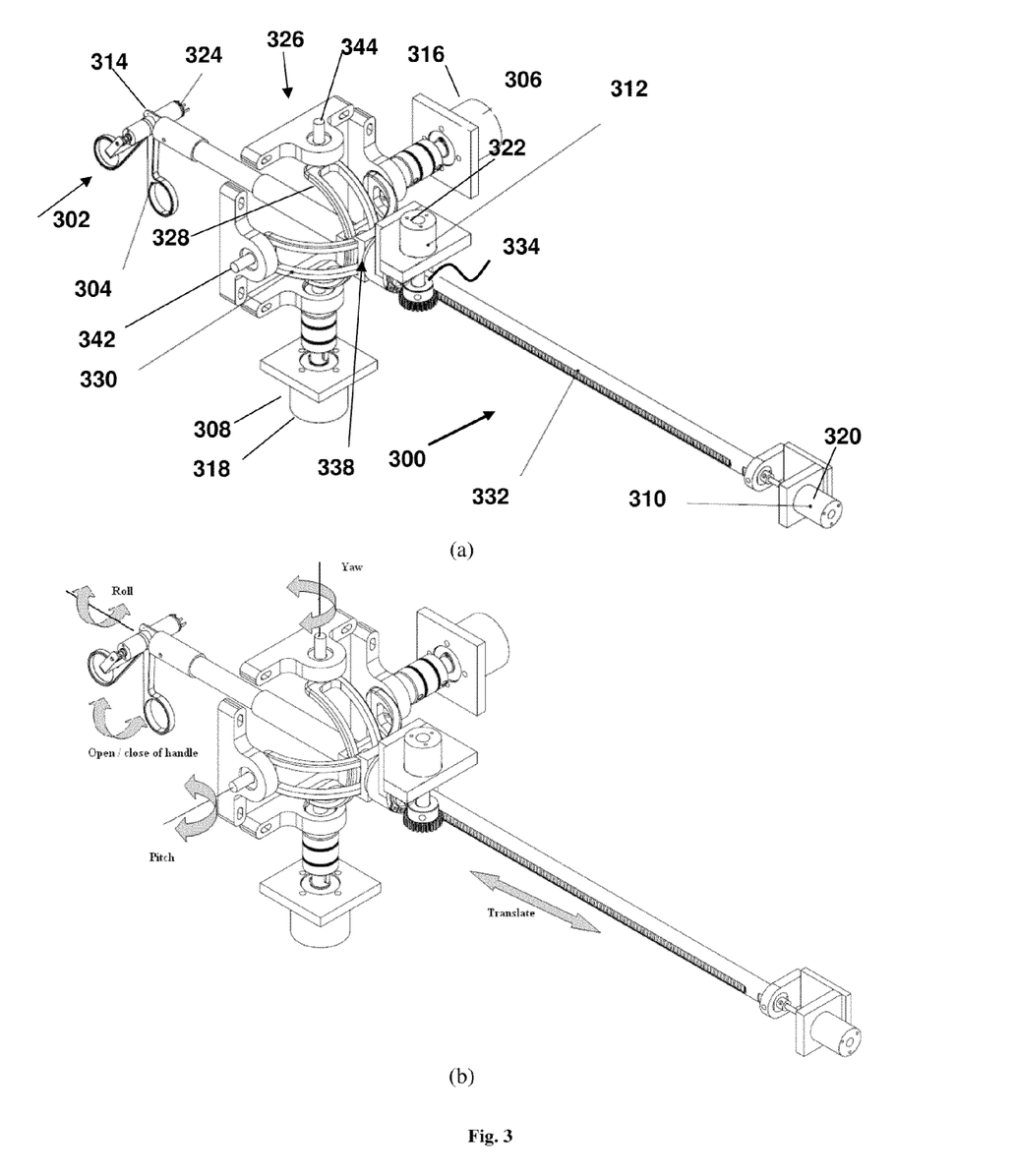
Figure 4:
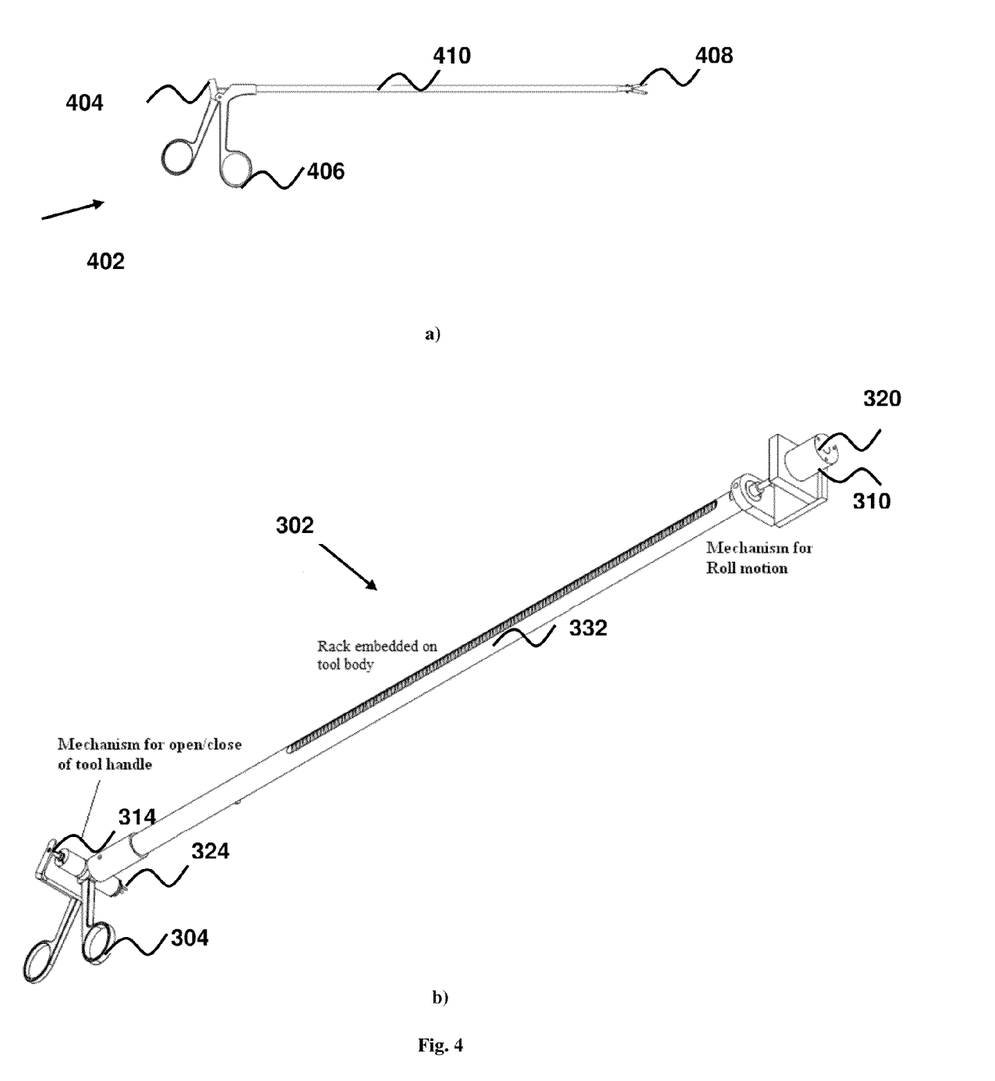

In FIG. 4 a), shows a normal laparoscopic surgical tool 402, including handle 406 applicator 408 and tool body 402, With reference to the normal surgical tool 402 in FIG. 4a), FIG. 4b) shows a hardware design of the component 302 in FIG. 3a of the robotic device according to an example embodiment, which is adapting motors and encoders to a normal surgical tool 402. The component 302 comprises the handle 304, the actuator (DC motor 314) and the sensor (an encoder 324) with an advantageous mechanism for controllable open/close of handle 406. Additionally, the component 302 also comprises an actuator (DC motor 310), a sensor (an encoder 320) with an advantageous mechanism for roll motion of tool. With the advantageous mechanism for open/close motion, the handle 304 can be open/closed by controlling the DC motor 314 and the open/close motion can be detected by the encoder 324 mounted on the DC motor 314. A rack 332 with an advantageous mechanism for translational motion embedded on tool body. The compoent 302 can be moved in translational motion, driven by the DC motor 312 (FIG. 3a)). The translational motion also can be detected by the encoder 322 (FIG. 3a)), mounted on the DC motor 312 (FIG. 3a)).

With the advantageous mechanism for roll motion, the component 302 can be rolled, driven by the DC motor 310. The roll motion also can be detected by the encoder 320, mounted on the DC motor 310. The actuator can be implemented in several forms, such as pneumatic, hydraulic power or electricity. The sensors are to acquire position and orientation information of the component 302. They can be, but are not limited to, encoder, orientation sensor and distance sensor in example embodiments.

Turning back to FIG. 3, there are four modes of operation for the robotic device 300, namely Record, Replay, Robotic assisted teaching, and Trainee mode. A patient specific anatomical model generated by image processing techniques is loaded in the Image-guided robot assisted surgical training system. All four operation modes work on the virtual patient specific anatomical model.

In the record mode, the robot 300 is passively operated by the master surgeon. A component 302 incorporated into the robot 300 is operated by the user manually. Motion of the component 302 is decoupled into roll, pitch, yaw, translation and open/close of handle 304. All this information is recorded to reconstruct the trajectory of the component 302. In order to provide the user with realistic sensation (haptic), a control system/controller is used to generate the sensation of tool-environment interaction based on the tissue's biomechanics model, in an example embodiment. In record mode, the rotatory encoders 316, 318, 320, 322 and 324 are detecting the motion of the master surgeon, and the DC motors 306, 308, 310, 312 and 314 are activated to provide haptic feedback, or to compensate frictional force.

In the replay mode, the robot 300 actively drives the component 302. The trainee surgeon can hold the handle 304 of the component 302, and follow the trajectory of the component 302 to learn the procedure of a recorded surgery. The DC motors 306, 308, 310, 312 and 314 and the rotatory encoders 316, 318, 320, 322 and 324 are activated to drive and ensure the component 302 moves in compliance with the motion recorded in the record mode.

The robotic assisted teaching mode is for a trainee surgeon who has gained confidence from the replay mode. The trainee surgeon is allowed to operate on the patient specific anatomical model with the surgical procedure learnt in the replay mode. The trajectory of the component 302 can be tracked by the rotatory encoders 316, 318, 320, 322 and 324. In the meantime, this trajectory can be compared to the trajectory acquired in the record mode, i.e. where the component 302 was operated by the master surgeon.

If the difference between the trajectory acquired from the trainee surgeon in the robot assisted teaching mode and the trajectory recorded in the record mode exceeds a predefined range, the robot could force the component 302 by way of the DC motors 306, 308, 310, 312 and 314, to follow the trajectory acquired in the record mode. In the robot assisted teaching mode, the trainee surgeon is given some freedom to perform the surgery with learnt procedures. In the robot assisted teaching mode, both DC motors and encoders are both switched on and in an active mode.

The trainee mode allows the trainee surgeon to operate on the anatomical model with the learnt surgical procedure on his/her own accord. The motion of the component 302 is recorded by the encoders 316, 318, 320, 322, and 324 for evaluation purpose. In this mode, the actuators (DC motors 306, 308, 310, 312, 314) incorporated in the robot 300 provide haptic feedback in the same manner as in the record mode. Therefore, in the trainee mode, both DC motors and encoders are switched on.

In the robot 300, a plurality of DC motors 306, 308, 310, 312, and 314 associated encoders 316, 318, 320, 322, and 324 are incorporated to implement 4 degrees of freedom (DOF), in addition to an open/close function of handle 304 of the component 302.

In this embodiment, DC motors and rotary encoders are chosen to work as the actuator and sensor respectively. With a rotary encoder mounted on a DC motor's shaft, the DC motors 306, 308, 310, 312, and 314 can be programmed to output tourque and rotation to drive the respective joints of the robot 300 to deliver accurate physical motion guidance to the trainee surgeon. At the same time, the rotatory encoders 316, 318, 320, 322, and 324 can acquire the trajectories of the respective joints when the DC motors 306, 308, 310, 312, and 324 are back driven in the record and the trainee modes.

A spherical mechanism 326 is incorporated into the robot 300 to decouple the orientation of the component 302 body into a spherical coordinate. The orientation of the component 302 body is expressed as pitch and yaw in terms of degree/radiant. The movement of the component 302 body drives to rotate the spherical arches 328, 330 at respective angels. The spherical arches 328, 330 are connected to the shafts of the DC motors 308, 306, and rotatory encoders 318, 316 are respectively mounted on the shaft ends of the DC motors 308, 306. The spherical mechanism comprises a base of the robotic device supporting the spherical arches 328, 330, the manual interface structure 302 and the translational and rotational mechanisms.

Figure 5:
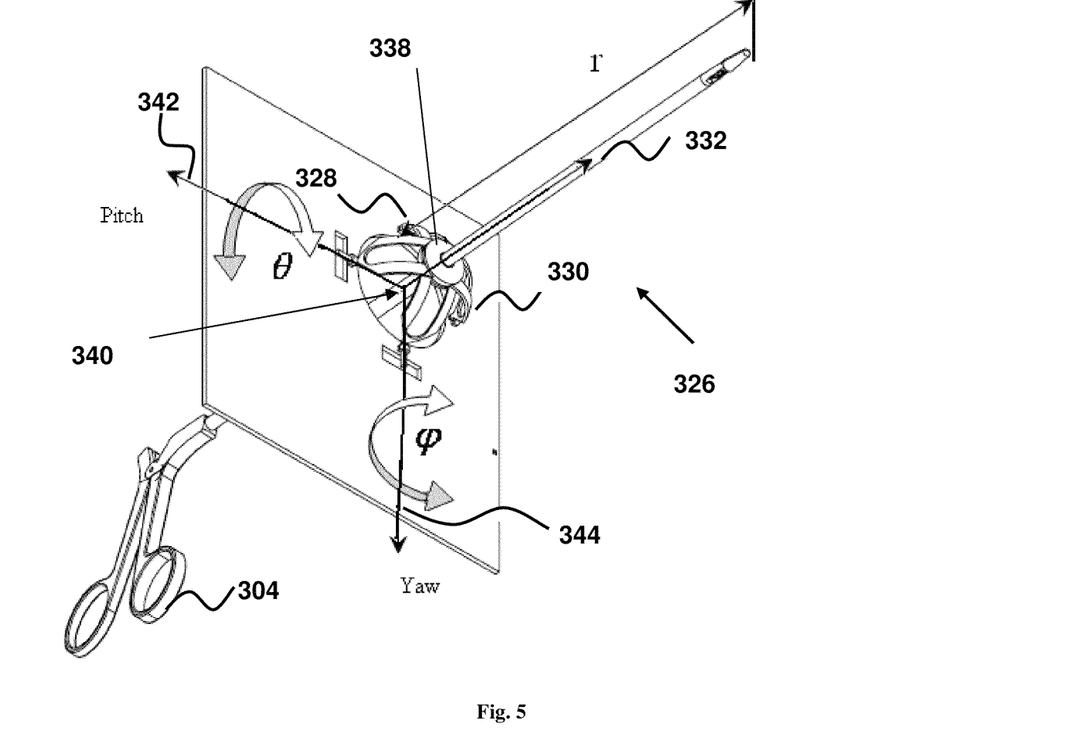
FIG. 5 shows a representation of tool tip in the spherical coordinate of the robotic device in a simplified drawing according to an example embodiment.

FIG. 5 illustrates the spherical mechanism 326 to decouple the orientation of component 302 into spatial coordinates in a simplified drawing according to an example embodiment. The orientation of the component 302 is expressed as pitch and yaw in terms of degree/radiant. The DC motors 306 (not shown in FIG. 5) drives to rotate the spherical arch 330 at angle θ and the DC motors 308 drives the spherical arch 328 at angle φ. In addition, the DC motor 312 (not shown in FIG. 5) drives the rack 332 and moves the handle 304 by a distance r, and the rotatory encoder 322 (not shown in FIG. 5), is mounted on the shaft of the DC motors 312 (not shown in FIG. 5). The spherical arche 328 are connected to shafts of DC motors 308 (not shown in FIG. 5), and rotary encoders 318 (not shown in FIG. 5) are mounted on the shafts of DC motor 308 (not shown in FIG. 5). The spherical arche 330 are connected to shafts of DC motors 306 (not shown in FIG. 5), and rotary encoders 316 (not shown in FIG. 5) are mounted on the shafts of DC motor 306. Hence the movement of the component 302 can be recorded by the rotary encoders 316, 318, 322. On the other hand, the movement of the component 302 can be driven by DC motors 306, 308, 312. The spherical mechanism 326 in the example embodiment, in employing the "inverted" spherical arches 328, 320 with the apex of the respective arches pointing away from the component 302 (and thus the user), is advantageously designed such that no part of the linkage can be exposed beyond the simulated incision point marked by the intersection 340 of the two pitch and yaw axes 342, 344. The intrusion of mechanical linkage into the user operational workspace is undesirable in a user-centric simulator. In other words, the linkage, here in the form of a slider 338, between the rotational mechanism, the rotational mechanism and the spherical mechanism, and the manual interface structure 302 are disposed on opposing sides of an intersection of a pitch axis 342 and a yaw axis 344 of the spherical mechanism.

Returning to FIG. 3, the slider 338 is moveable within the spherical arches 328, 330 and is configured to couple the shaft 332 to the first and second spherical arches 328 and 330. The slider 338 is configured to enable rotational and translational movement of the shaft 332 relative to the spherical arches 328, 330. A mechanism for translational motion of the component 302 is implemented by DC motors 312, and the motion can be tracked by rotatory encoders 322 mounted on the DC motor 312. The DC motor 312 and associated encoder 322 are incorporated in the robot 300 to provide a mechanism for translational movement of the component 302. Rack and pinion can be applied to obtain the transformed of the translational motion. The mechanism for translational motion is described in detail in FIG. 6.

Figure 6:
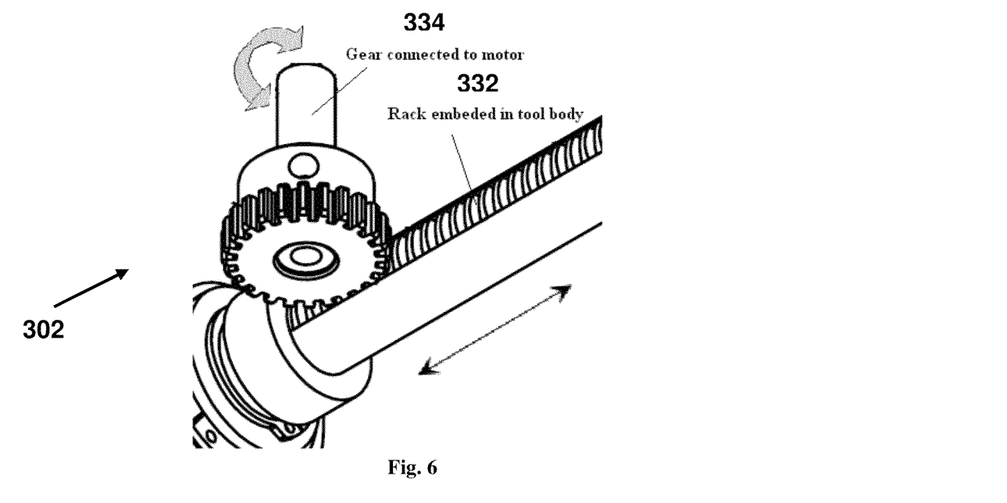
FIG. 6 shows translational movement of a component of the robotic device according to an example embodiment.

FIG. 6 shows translational movement of the component 302 of the robotic device according to an example embodiment. The translational movement mechanism can be driven by DC motors 312 (not shown in FIG. 6) and the motion can be tracked by rotary encoders 322 (not shown in FIG. 6), in which a gear 334 can be connected to the DC motor 312 (not shown in FIG. 6). The gear teeth of the gear 334 engage the teeth of the pinions of the rack 332, which is embedded in the component 302 and they can be applied to obtain the transform of translational motion.

Turning back to FIG. 3, a mechanism for rotational motion of the component 302 is implemented by DC motors 310, and the motion can be tracked by rotatory encoders 320. The DC motor 310 and associated encoder 320 are incorporated in the component 302 300 to provide a mechanism for rotatory motion of the component 302. The mechanism for rotatory motion is described in detail in FIG. 7.

Figure 7:
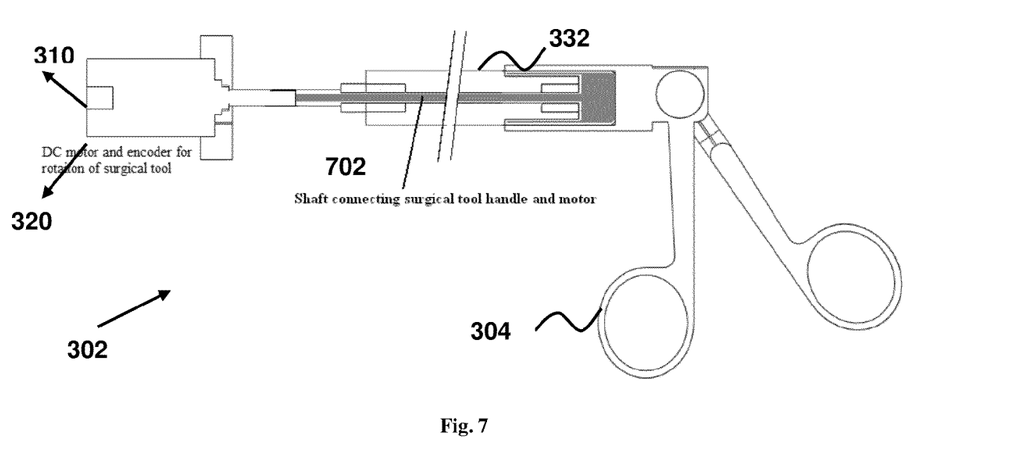
FIG. 7 shows rotational movement of a component of the robotic device according to an example embodiment.

FIG. 7 shows a rotation of the component 302 of the robotic device 300 according to an example embodiment. The mechanism can be driven by DC motors 310, in which a shaft 702 (inside the rack 332) connects the handle 304 and the DC motor 310, and the motion can be tracked by rotary encoder 320, which is mounted on the DC motor 310.

All the actuators (DC motors), sensors (encoders) can be connected with a controller 204 such as, but not limited to, a backend server, a personal computer, a laptop, a mobile phone, a PDA via such as, but not limited to, 3G, cable, WiFi, Bluetooth.

For completeness, available materials can be used to fabricate components of the disclosed mechanisms. In many example embodiments, the rack 332, the handle 304, the spherical arches 328, 330 can be fabricated from, for example, iron, steel, stainless steel, copper, silver, etc. In addition, manufacturing techniques can be used to fabricate the components such as the spherical arches 328, 330, but not limited to, by molding, shaping, casting and punching.

Figure 8:
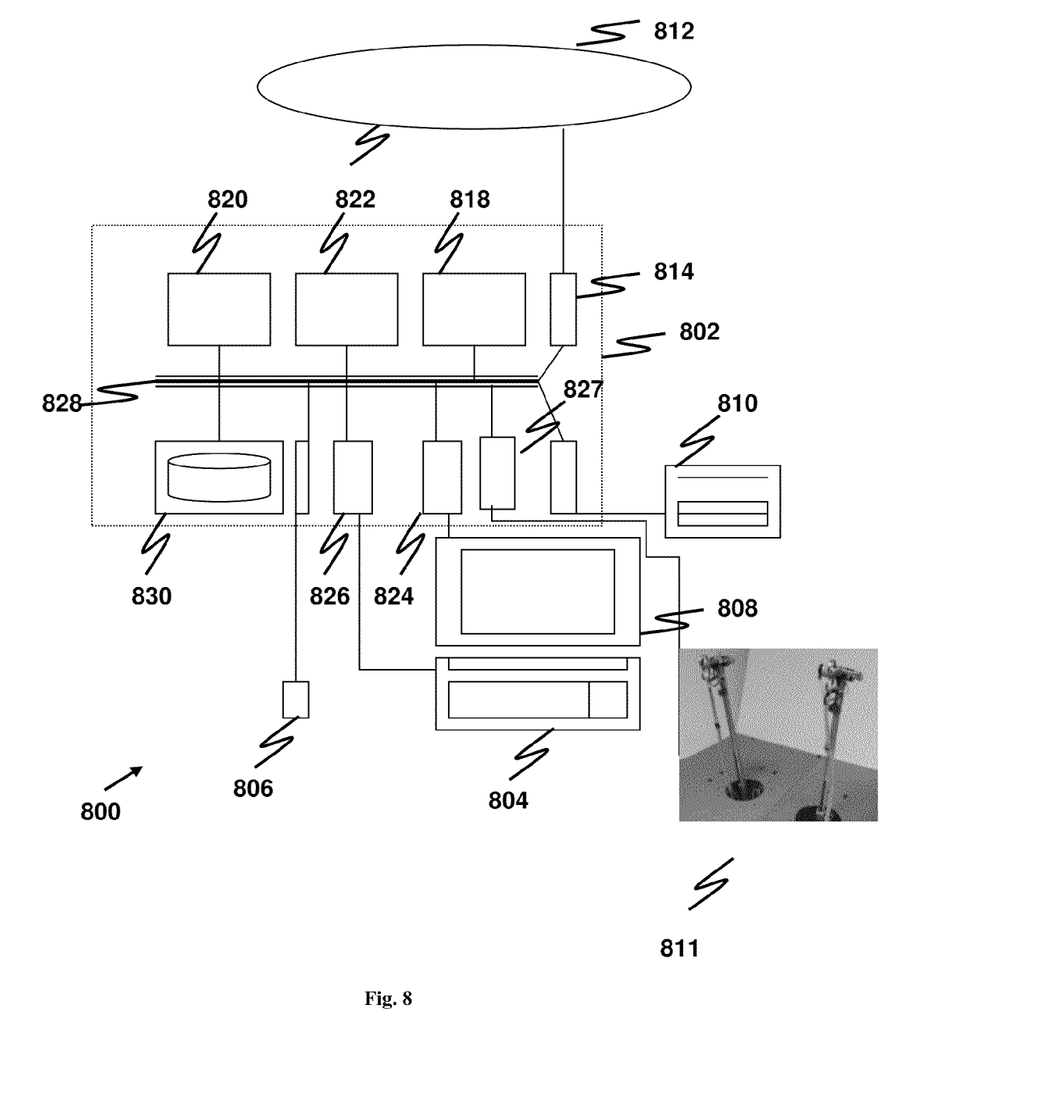
FIG. 8 illustrates a computer system upon which the method and system of the example embodiments can be implemented.

The robotic device for use in image-guided robot assisted surgical training of the example embodiments can be coupled to a computer system 800, schematically shown in FIG. 8 for implementation in an image-guided robot assisted surgical training system and method. The system and method may be implemented as software, such as a computer program being executed within the computer system 800, and instructing the computer system 800 to conduct the method of the example embodiment.

The computer system 800 comprises a computer module 802, input modules such as a keyboard 804 and mouse 806 and a plurality of input and/or output devices such as a display 808, printer 810, and robot arm 811.

The computer module 802 is connected to a computer network 812 via a suitable transceiver device 814, to enable access to e.g. the Internet or other network systems such as Local Area Network (LAN) or Wide Area Network (WAN).

The computer module 802 in the example includes a processor 818, a Random Access Memory (RAM) 820 and a Read Only Memory (ROM) 822. The computer module 802 also includes a number of Input/Output (I/O) interfaces, for example I/O interface 824 to the display 808, I/O interface 826 to the keyboard 804, and I/O interface 827 to robot arm 811.

The components of the computer module 802 typically communicate via an interconnected bus 828 and in a manner known to the person skilled in the relevant art.

The application program is typically supplied to the user of the computer system 800 encoded on a data storage medium such as a CD-ROM or flash memory carrier and read utilising a corresponding data storage medium drive of a data storage device 830. The application program is read and controlled in its execution by the processor 818. Intermediate storage of program data maybe accomplished using RAM 820.

The robotic device in example embodiments can deliver surgical training with active motion guidance. This can be achieved by the example embodiments of the invention in design and implementation methodology. For example, example embodiments employ a mechanism that minimizes parasitic back driven force while preferably maintaining structural stability and can accommodate a high output resolution motor through appropriate mechanism design.

Example embodiments can provide a specialized spherical manipulator. In laparoscopic surgery, the surgical tool pivots about the insertion point at the surface of abdominal. The constraint of the insertion point reduces the mobility of the surgical tool to 4 DOF in addition to one DOF on the open/close task of handle 304 of component 302 (compare FIG. 3a)). The spherical mechanism, shown in FIG. 5, is employed to implement 3 axes of control. The positioning of the tool tip can be simply represented in a spherical coordinate with angle θ, φ and length r (See illustration in FIG. 5) in example embodiments. The position of surgical tool handle can be known through rigid transformation. This preferably facilitates the establishment of a closed form inverse kinematics model which is advantageous in the implementation of the control algorithm. Unlike existing serial manipulators, example embodiments do not require numerous iterations based on a numerical inverse kinematic approach. Example embodiments are analytical as a result of the closed form solvable inverse kinematics. This preferably allows a model based control scheme which facilitates the implementation of virtual reality simulation and integration of a haptic interface. In addition, the proposed spherical mechanism is an inverted spherical mechanism. The mechanical linkage is beneath the point of pivotal and hence isolated from the user for all configurations of the pitch and yaw motion. Also, the spherical mechanism in example embodiments requires only spherical two arches and a sliding block, advantageously making the spherical mechanism robust and compact.

Example embodiments contribute to the effectiveness in implementation of a surgical training method and system. The example embodiments exploit the sensory and actuation components to operate differently in each mode. The implementation of recording and replaying in example embodiments uses coupled rotary encoders and DC motors. Each rotary encoder generates a digital signal due to the motion of the surgical tool. The DC motors with rotary encoders as a feedback device in the example embodiments can be programmed to drive the mechanical part of the robot. The rotary encoders work in the joint space domain. Since both the sensor and actuator work in the joint space domain, there is preferably no need for kinematics transformation for recording and replaying application. This can reduce the computational complexity and can improve timing performance through task specific implementation.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A robotic device for use in image-guided robot assisted surgical training, the robotic device comprising:
   a manual interface structure configured to simulate handling of a surgical tool;
   a translational mechanism for translational motion of the manual interface structure;
   a rotational mechanism for rotational motion of the manual interface structure; and
   a spherical mechanism configured to decouple the orientation of the manual interface structure into spatial coordinates,
   wherein a linkage and the manual interface structure are disposed on opposing sides of an intersection of a pitch axis and a yaw axis of the spherical mechanism, wherein the linkage is a link between the rotational mechanism, the translational mechanism and the spherical mechanism.

2. The robotic device according to claim 1, wherein the spherical mechanism comprises first and second substantially orthogonal rotatable spherical arches, wherein movement of the manual interface structure drives the first and second spherical arches.

3. The robotic device according to claims 2, wherein the spherical mechanism comprises first and second pairs of an actuator and a sensor for each of the first and second arches.

4. The robotic device according to claim 1, wherein the translational mechanism comprises a third pair of an actuator and a sensor.

5. The robotic device according to claim 1, wherein the rotational mechanism comprises a fourth pair of an actuator and a sensor.

6. The robotic device according to claim 1, wherein the manual user interface comprises an open-and-close mechanism to simulate opening and closing of the surgical tool.

7. The robotic device according to claim 6, wherein the open-and-close mechanism comprises a fifth pair of an actuator and a sensor.

8. The robotic device according to claim 3, wherein the sensors are configured to record operation of the manual interface structure by a user.

9. The robotic device according to claim 3, wherein the actuators are configured to drive the manual interface to reproduce a recorded operation of the manual interface structure.

10. The robotic device according to claim 1, wherein the manual interface structure comprises a shaft coupled to each of the translational, rotational, and spherical mechanisms.

11. The robotic device as claimed in claim 10, wherein the linkage comprises a slider moveable within a first and a second spherical arch and configured to couple the shaft to the first and second spherical arches.

12. The robotic device according to claim 11, wherein the slider is configured to enable rotational and translational movement of the shaft relative to the first and second spherical arches.

13. The robotic device as claimed in claim 10, wherein the shaft is coupled to the translational mechanism by way of a track and gear coupling.

14. The robotic device as claimed in claim 10, wherein the shaft is coupled to a rotational axis of the rotational mechanism.

15. The robotic device according to claim 1, wherein the spherical mechanism comprises a base of the robotic device supporting a first and a second spherical arch, the manual interface structure and the translational and rotational mechanisms.

* * * * *